US00PP28704P3

(12) United States Plant Patent
Suphachadiwong

(10) Patent No.: US PP28,704 P3
(45) Date of Patent: Nov. 28, 2017

(54) *VANDA* PLANT NAMED 'SPCDW1506'

(50) Latin Name: ***Vanda* Jones ex R. Br.**
Varietal Denomination: SPCDW1506

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 26 days.

(21) Appl. No.: 14/999,701

(22) Filed: Jun. 16, 2016

(65) Prior Publication Data

US 2016/0374250 P1 Dec. 22, 2016

(30) Foreign Application Priority Data

Jun. 19, 2015 (QZ) ..... PBR 2015/1386

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Vanda* cultivar named 'SPCDW1506' which is characterized by flowers with a dark yellow to somewhat peach base color and an overlaying irregular tessellation pattern comprised of a coalescence of greyed-purple blurred dots and blotches, highly ruffled sepal and petal margins, and the stability of these characteristics from generation to generation.

3 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1506'.

CROSS REFERENCE TO RELATED APPLICATIONS

This application claims priority to the Community Plant Variety Rights application number 2015/1386, filed Jun. 19, 2015, which is herein incorporated by reference.

BACKGROUND OF THE INVENTION

Parentage: The *Vanda* variety 'SPCDW1506' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in June of 1995.

The new variety was first selected in December of 2000, in a research greenhouse in Bangphra, Thailand belonging to the inventor. After identifying the new variety as a potentially interesting selection, the inventor continued confidential testing and propagation of 'SPCDW1506', assessing stability of the unique characteristics of this variety.

Asexual Reproduction: Asexual reproduction of the new cultivar 'SPCDW1506', by way of mericloning, was first initiated in December of 2009 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1506' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1506'. These characteristics in combination distinguish 'SPCDW1506' as a new and distinct *Vanda* cultivar:

1. *Vanda* 'SPCDW1506' exhibits sepals and petals with a dark yellow to somewhat peach base color; and
2. *Vanda* 'SPCDW1506' exhibits sepals and petals with an overlaying irregular tessellation pattern comprised of a coalescence of greyed-purple blurred dots and blotches; and
3. *Vanda* 'SPCDW1506' exhibits sepals and petals with highly ruffled margins.

BOTANICAL DESCRIPTION OF THE PLANT

Figure 1:
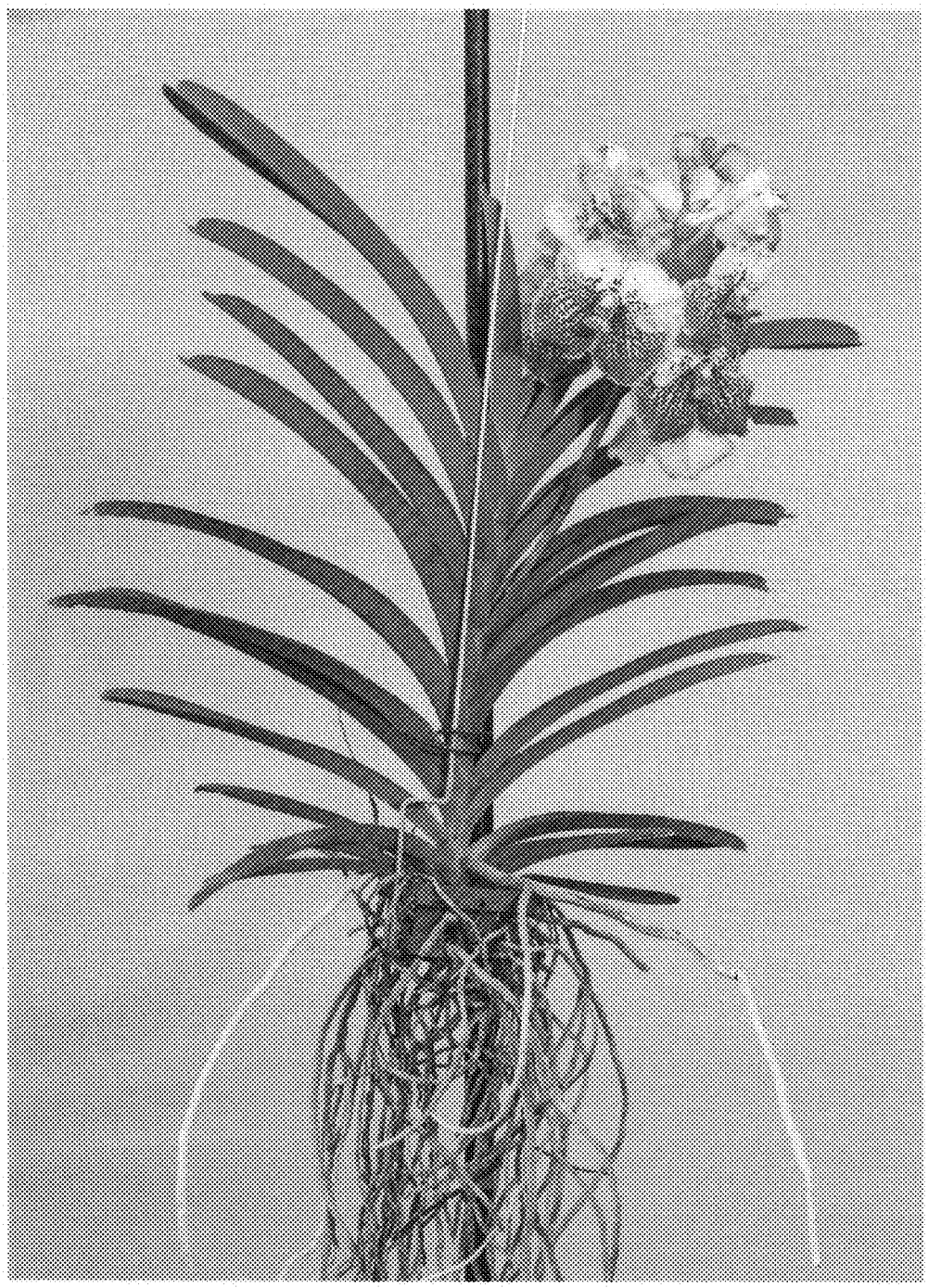
FIG. 1 illustrates, as nearly true as it is reasonably possible to make the same in color photographs of this type, an exemplary plant of 'SPCDW1506' grown in a commercial greenhouse in Honselersdijk, the Netherlands. This plant is approximately 6 years old from the time of mericloning, shown planted in an 8 by 8 cm container.
Figure 2:
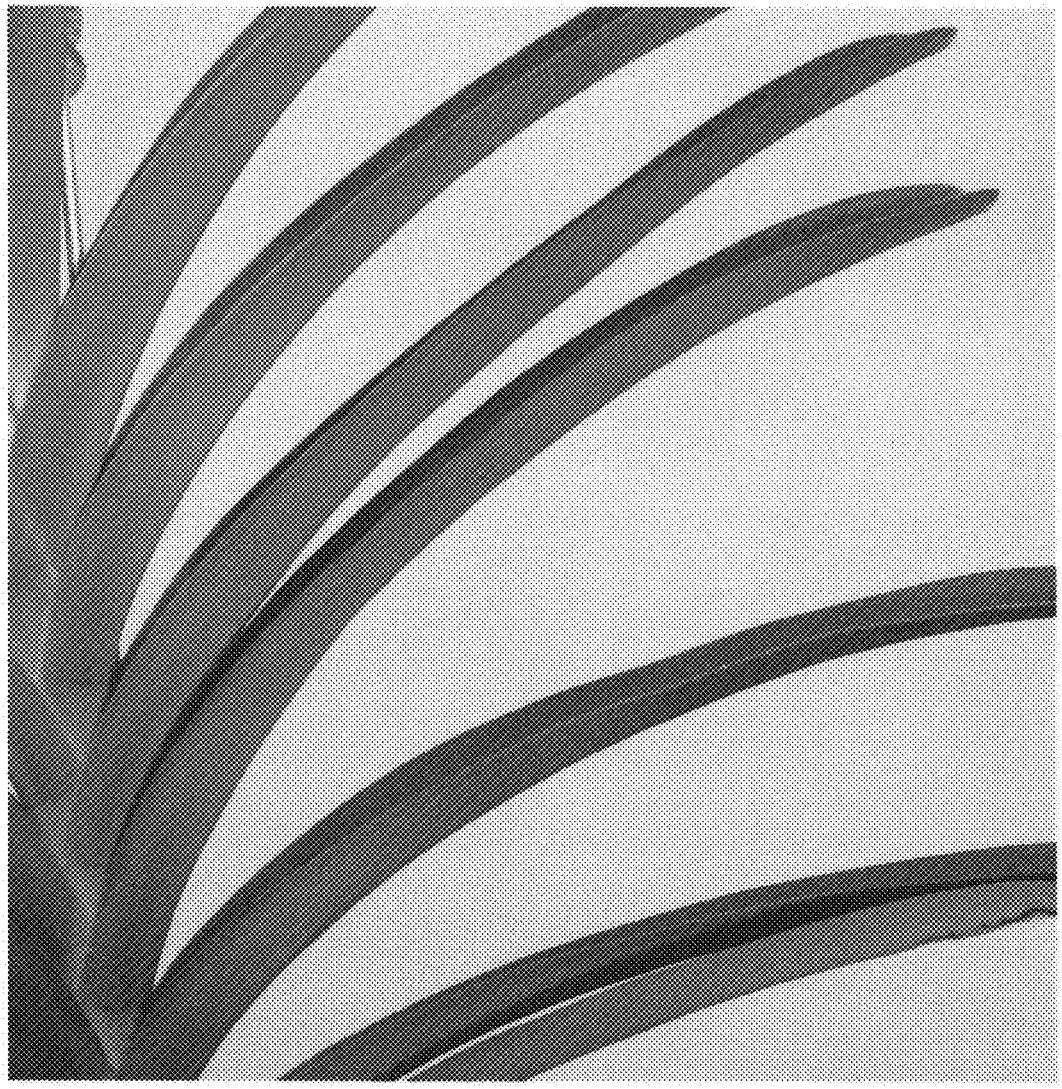
FIG. 2 illustrates, as nearly true as it is reasonably possible to make the same in color photographs of this type, the typical foliage of 'SPCDW1506'.
Figure 3:
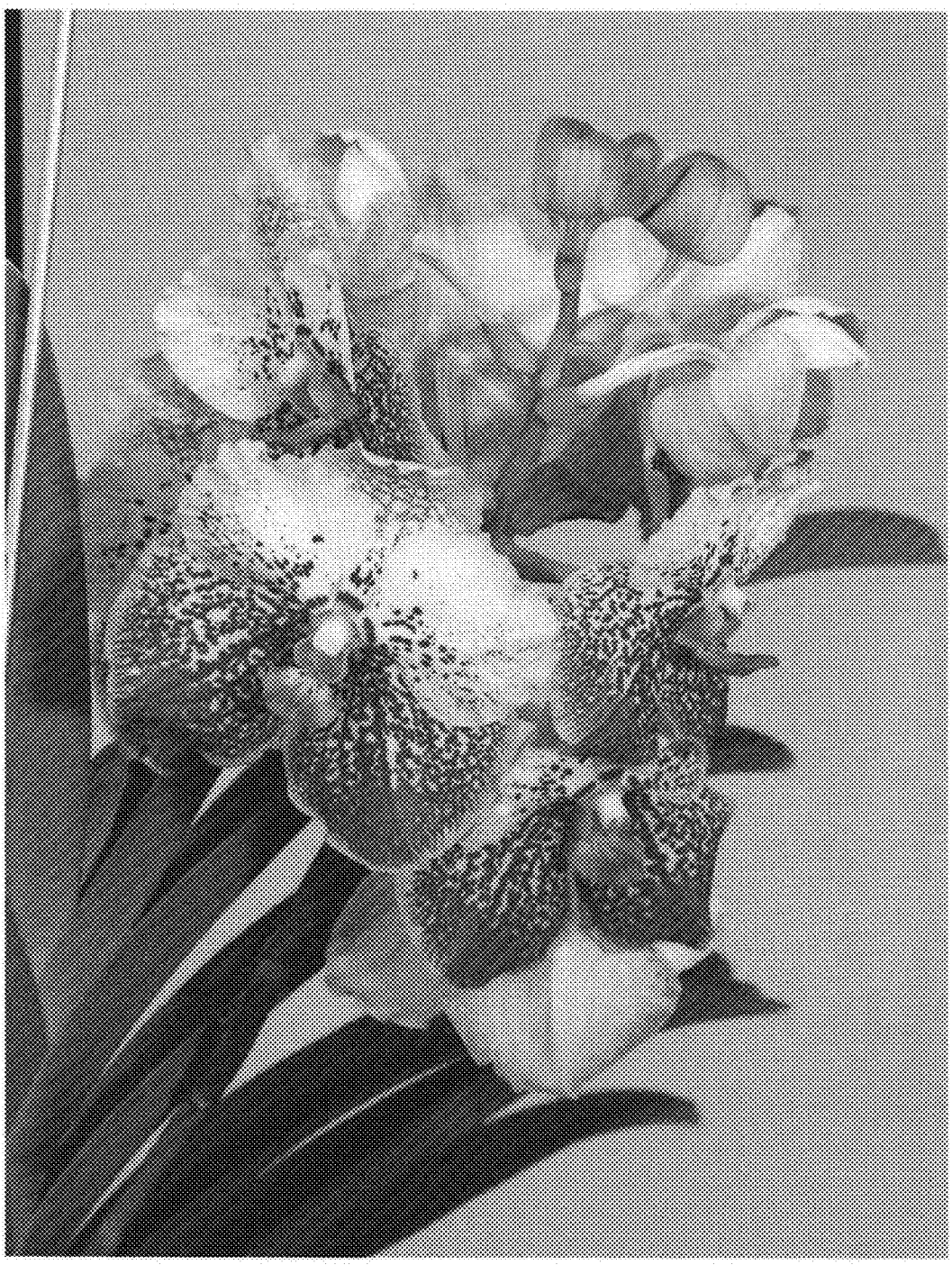
FIG. 3 illustrates, as nearly true as it is reasonably possible to make the same in color photographs of this type, the typical inflorescence and flower of 'SPCDW1506'.

The following observations and measurements made in April of 2016 describe averages from a sample set of six specimens of six year-old 'SPCDW1506' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1506' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'SPCDW1506' and comparisons with other varieties of *Vanda* are provided below.

Plant description:

- *Growth habit.*—Perennial; monopodial, upright. Single monopodial leafy stem, with flowers carried slightly above the leaf plane, inflorescences grow from the leaf axils.
- *Average height from base (plant grown in hanging basket, so no soil line present) to foliar plane.*—46.7 cm.
- *Average height from base (plant grown in hanging basket, so no soil line present) to top of floral plane.*—49.0 cm.
- *Plant spread.*—Average of 44.3 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—67.8 cm long with a diameter of 0.4 cm, on average.
- *Texture.*—Very fleshy; non-fibrous.
- *Color.*—Greyed-Green, near RHS 192B to 192C; root apex is yellow-green, RHS 147B to 147C.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—26.2 cm.
- *Diameter.*—0.9 cm.
- *Internode length.*—1.3 cm.
- *Luster.*—Matte.
- *Aspect.*—Near vertical.
- *Strength.*—Very strong.
- *Color, juvenile.*—Yellow-green, near RHS 150D.
- *Color, mature.*—Yellow-green, near RHS 150D.
- *Color at internodes.*—Yellow-green, near RHS150D.
- *Pubescence.*—Glabrous.

Foliage:

- *Arrangement.*—Distichous.
- *Quantity.*—Approximately 26 leaves per plant.
- *Dimensions.*—30.0 cm long and 2.6 cm wide, on average.
- *Shape of blade.*—Ligulate; moderately carinate.
- *Aspect.*—Slightly curved.
- *Apex.*—Unequal praemorse.
- *Base.*—Sheathing.
- *Sheath dimensions.*—4.0 cm long and 1.6 cm wide, on average.
- *Sheath color.*—Yellow-green, near RHS 154D.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Juvenile foliage, adaxial surface — Yellow-green, near RHS 144A, and green towards the margins, near RHS 143A. Juvenile foliage, abaxial surface — Green, near RHS 143B, and darker towards the margins, near 137B. Mature foliage, adaxial surface — Green, near RHS 137B. Mature foliage, abaxial surface — Yellow-green, near RHS 144A, and green towards the margins, near RHS 143A.
- *Venation.*—Parallel.
- *Venation color, adaxial surface.*—Green, near RHS 137B.
- *Venation color, abaxial surface.*—Yellow-green, near RHS 144A, and green towards the margins, near RHS 143A.
- *Petiole.*—No petioles present, leaves sessile.

Inflorescence:

- *Inflorscence arrangement.*—Axially placed raceme.
- *Natural flowering season.*—Autumn into winter.
- *Time to flower.*—Approximately 10 months.
- *Flowers per inflorescence.*—Average of 14; 11 open flowers and 3 buds.

*Inflorescence height.*—Approximately 21.7 cm (measured from base of lowest flower to top of upper flower).

*Inflorescence diameter.*—Approximately 17.7 cm.

*Peduncle.*—Dimensions — Approximately 34.7 cm long and 0.6 cm wide. Aspect — Generally at a 30 degree angle to lateral branch axis. Strength—Moderately strong. Texture and luster — Glabrous and moderately glossy. Color — Yellow-green, RHS 144A.

Bud:

*Length.*—Average of 1.8 cm.

*Diameter.*—Average horizontal diameter is 1.9 cm; the vertical diameter is 2.0 mm.

*Shape.*—Cubic, with a deltoid apex which is pointed downward.

*Pubescence, texture and luster.*—Glabrous, smooth and matte.

*Color.*—Yellow-green, near RHS 150B to 150C; apex is darker, near RHS 152C to 152D.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 9.5 cm.

*Diameter.*—Approximately 8.8 cm.

*Depth.*—Approximately 3.5 cm.

*Fragrance.*—No fragrance.

*Lastingness.*—6 to 8 weeks, on average.

*Persistent.*—Self-cleaning.

*Petals.*—Quantity of Petals — 3 unfused petals; two conventional petals and one labellum. Arrangement — One lateral petal on each side. Length — Approximately 4.0 cm. Width — Approximately 4.3 cm. Shape — Reniform to near orbicular. Apex — Obtuse. Base — Cuneate. Margin — Entire; highly undulated. Pubescence, texture and luster of upper surface — Glabrous, velvety and matte. Pubescence, texture and luster of lower surface — Glabrous, velvety and matte. Color when opening, upper surface — Yellow, near RHS 2D; petals are slightly dotted greyed-purple, near RHS 183A to 183B. Color when opening, lower surface — Yellow, near RHS 2D; dots from upper surface can be seen from the lower surface; near RHS 182C to 182D. Color when fully opened, upper surface — Yellow, near RHS 2D; margins tinged greyed-yellow, near RHS 162C to 162D; petals are moderately dotted greyed-purple, near RHS 183A to 183B, particularly on the lower half. Color when fully opened, lower surface — Yellow, near RHS 2D; margins tinged greyed-yellow, near RHS 162C to 162D; dots from upper surface can be seen from the lower surface; near RHS 182C to 182D. Fading, upper surface — Not fading. Fading, lower surface — Not fading. Venation — Reticulate. Venation color, fully opened, upper surface — Yellow, near RHS 2D; margins tinged greyed-yellow, near RHS 162C to 162D. Venation color, fully opened, lower surface — Yellow, near RHS 2D; margins tinged greyed-yellow, near RHS 162C to 162D.

*Labellum.*—Shape — Three-lobed, lateral lobes are ovate and involute; central lobe is flat and near deltoid. Length — Central lobe — Approximately 1.8 cm. Lateral lobes — Approximately 0.8 cm. Width — Central lobe — Approximately 1.7 cm. Lateral lobes — Approximately 0.8 cm. Apex, central lobe — Slightly emarginate. Apex, lateral lobes — Obtuse. Base, central and lateral lobes — Cuneate. Margin, central lobe — Slightly irregular; undeeply angulate; not undulate. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Greyed-orange, near RHS 173B, and fading to yellow-green towards the base, RHS 1C to 1D. Lateral lobes — Yellow-green, near RHS 151D, and finely dotted greyed-orange, near RHS 166D; base tinged darker, near 166C. Color when opening, lower surface — Central lobe — Greyed-orange, near RHS 165C, and fading to yellow-green towards the base, near RHS 150C; slightly blotched greyed-red at the margins, near RHS 178B. Lateral lobes — Yellow-green, near RHS 151 D, and very finely dotted greyed-orange, near RHS 165D. Color when fully opened, upper surface — Central lobe — Greyed-orange, near RHS 174B, and fading to yellow towards the base, near RHS 3C. Lateral lobes — Yellow-green, near RHS 151 D, and very finely dotted greyed-orange, near RHS 165D; base tinged darker, near 166C. Color when fully opened, lower surface — Central lobe — Greyed-orange, near RHS 165C, and fading to yellow-green towards the base, RHS 150B to 150C; slightly blotched greyed-red at the margins, near RHS 178B. Lateral lobes — Yellow-green, near RHS 151 D, and very finely dotted greyed-orange, near RHS 165D. Fading, upper surface — Not fading. Fading, lower surface — Not fading. Venation — No veins visible. Venation color, fully opened, upper surface — Central lobe — No veins visible. Lateral lobes — No veins visible. Venation color, fully opened, lower surface — Central lobe — No veins visible. Lateral lobes — No veins visible.

*Callosities.*—Dimensions — 1.4 cm long and 0.7 cm wide, on average. Color — Yellow, near RHS 3C.

*Spurs.*—Quantity — Average of 1. Length — Approximately 0.7 cm. Diameter — Approximately 0.4 cm. Vertical height — Approximately 0.7 cm, at the base. Shape — Short triangular. Apex — Bluntly acute. Base — Broad Cuneate. Pubescence, texture and luster — Glabrous, smooth, and matte. Color — Yellow-green, near 154D.

*Sepals.*—Quantity — Average of 3 unfused sepals. Arrangement — One dorsal sepal and two lateral sepals. Length — Dorsal sepal — Approximately 4.7 cm. Lateral sepals — Approximately 5.1 cm. Width — Dorsal sepal — Approximately 4.6 cm. Lateral sepals — Approximately 5.8 cm. Shape — Dorsal sepal — Broad ovate. Lateral sepals — Reniform. Apex, dorsal and lateral sepals — Obtuse. Base, dorsal and lateral sepals — Cuneate. Margin, dorsal and lateral sepals — Entire; dorsal sepals are moderately undulated and lateral sepals are slightly undulate. Pubescence, texture and luster — Glabrous, velvety, and matte on both the upper and lower sepal surfaces. Color when opening, upper surface — Dorsal sepal — Yellow, near RHS 2D; slightly dotted greyed-purple, near RHS 183A to 183B. Lateral sepals — Yellow-green, near RHS 154B to 154C, and fading to greyed-yellow towards the margins and apex, near RHS 160B; heavily dotted greyed-purple, near RHS 183A to 183B. Color when opening, lower surface — Dorsal sepal — Yellow, near RHS 2D; dots from upper surface can be seen from the lower surface; near RHS 182C to 182D. Lateral sepals — Yellow-green, near RHS 154B to 154C, and fading to greyed-yellow towards the margins and apex, near RHS 160A to 160B. Color when fully opened, upper surface — Dorsal sepal — Yellow, near RHS 2D; margins are tinged greyed-yellow, near RHS 162C; strongly dotted greyed-purple, near RHS 183A. Lateral sepals — Yellow-green, near RHS 154C, and fading to greyed-yellow towards the margins and apex, near RHS 160B; heavily dotted greyed-purple, near RHS 183B to 183C. Color when fully opened, lower surface — Dorsal sepal — Yellow, near RHS 2D; margins are tinged greyed-yellow, near RHS 162C to 162D; dots from upper surface can be seen from the lower surface; near RHS 182C to 182D. Lateral sepals — Yellow-green, near RHS 154C to 154D, and fading to greyed-yellow towards the margins and apex, RHS 160A to 160B. Fading, upper surface — The color of all sepals does not fade. Fading, lower surface — The color of all sepals does not fade. Venation — Reticulate. Venation color, fully opened, upper surface — Dorsal sepal — Greyed-red, RHS 181B to 181C. Lateral sepals — Greyed-purple, RHS 183B to 183C. Venation color, fully opened, lower surface — Dorsal sepal — Greyed-yellow, near RHS 162D. Lateral sepals — Greyed-yellow, near RHS 162D.

*Pedicels.*—Length — Approximately 5.5 cm. Diameter — Approximately 0.4 cm. Angle — Approximately 80 degree angle to peduncle axis. Strength — Moderate. Texture — Glabrous, axially angled with 5 "ribs", axially twisted (due to resupination). Luster — Glossy. Color — Yellow-green, near RHS 145D, and darker towards the proximal end, near RHS 154A.

*Bract.*—Quantity — One bract present at the base of each pedicel. Shape — Obovate; folded around the base of each pedicel. Dimensions — Average of 1.6 cm long and 1.2 cm wide. Apex — Broad acute. Base — Broad cuneate. Margins — Entire. Color, both surfaces — Yellow-green, in between RHS 145C and 146D. Texture — Sticky to the touch.

Reproductive Organs:

*Column.*—Length — Approximately 0.6 cm. Diameter — Approximately 0.6 cm. Color — Yellow-green RHS 154C.

*Ovary.*—Position — Inferior. Diameter — Approximately 1.2 cm. Color — Yellow-green RHS 150D.

*Pollinia color.*—Yellow RHS 13A.

Seed and fruit: No fruit and seed production has been detected to date.

COMPARISON WITH THE PARENT PLANTS

Plants of the new cultivar 'SPCDW1506' differ from the unnamed *Vanda* seed parent (not patented) by the characteristics described in Chart 1.

CHART 1

| Characteristic | 'SPCDW1506' | Unnamed seed parent |
|---|---|---|
| Color pattern on the petals and sepals. | Irregular tessellation comprised of a coalescence of blurred dots and blotches. | No pattern is present. |
| Flower size. | Smaller flowers than seed parent. | Larger flowers than 'SPCDW1506'. |
| Quantity of flowers per inflorescence. | More flowers than seed parent. | Less flowers than 'SPCDW1506'. |
| Floriferousness. | More floriferous than seed parent. | Less floriferous than 'SPCDW1506'. |

Plants of the new cultivar 'SPCDW1506' differ from the unnamed *Vanda* pollen parent (not patented) by the characteristics described in Chart 2.

CHART 2

| Characteristic | 'SPCDW1506' | Unnamed pollen parent |
|---|---|---|
| Color pattern on the petals and sepals. | Irregular tessellation comprised of a coalescence of blurred dots and blotches. | Lightly dotted. |
| Flower size. | Much larger flowers than pollen parent. | Much smaller flowers than 'SPCDW1506'. |
| General plant size. | Larger overall plant size than the pollen parent. | Smaller overall plant size than 'SPCDW1506'. |

COMPARISON WITH THE MOST SIMILAR *VANDA* CULTIVAR KNOWN TO THE INVENTOR

Plants of the new cultivar 'SPCDW1506' are most similar to the cultivar, *Vanda* 'SPGDW1406' (U.S. Plant Pat. No. 28,324). A comparison of 'SPCDW1506' with *Vanda* 'SPCDW1406' is described in Chart 3.

CHART 3

| Characteristic | 'SPCDW1506' | 'SPCDW1406' |
|---|---|---|
| General tonality of the background color of the flowers. | Somewhat peach colored. | Light yellow. |
| Brightness of petal and sepal coloration. | Overall, much darker. | Overall, much less dark. |
| Expression of the color pattern on petals and sepals. | Much more prominent. | Much less prominent. |
| Color pattern on the petals and sepals. | Irregular tessellation comprised of a coalescence of blurred dots and blotches | Primarily comprised of individual dots. |
| Shape of labellum. | More broad than 'SPCDW1406'. | Less broad than 'SPCDW1506'. |
| Undulation of petal and sepal margins. | More highly undulated. | Less undulation. |

That which is claimed is:

1. A new and distinct variety of *Vanda* plant named 'SPCDW1506', substantially as described and illustrated herein.

* * * * *